United States Patent [19]
Belkin et al.

[11] Patent Number: 5,510,329
[45] Date of Patent: Apr. 23, 1996

[54] PREPARATIONS FOR THE TREATMENT OF EYES

[75] Inventors: Michael Belkin; Naphtali Savion, both of Givat Shmuel; Nahum Landshman, Tel Aviv, all of Israel

[73] Assignee: Ramot University for Applied Research and Industrial Development Ltd., Tel Aviv, Israel

[21] Appl. No.: 997,664

[22] Filed: Dec. 28, 1992

Related U.S. Application Data

[63] Continuation of Ser. No. 673,867, Mar. 22, 1991, abandoned, which is a continuation of Ser. No. 185,893, Apr. 26, 1988, abandoned.

[51] Int. Cl.$^6$ ............................................ A61K 38/00
[52] U.S. Cl. .................................................... 514/12
[58] Field of Search ................................................ 514/12

[56] References Cited

U.S. PATENT DOCUMENTS 4,141,973  2/1979  Balazs ........................................ 514/54

FOREIGN PATENT DOCUMENTS

| | | |
|---|---|---|
| 0138572 | 4/1985 | European Pat. Off. . |
| 0136782A2 | 4/1985 | European Pat. Off. . |
| 0136782 | 4/1985 | European Pat. Off. . |
| 62-122671 | 3/1987 | Japan . |
| 0122671 | 6/1987 | Japan . |

OTHER PUBLICATIONS

Sanion, *Metab. Pediat. Syst. Ophthal.*, 6, 305, 1982.
Lee, *Journal of Pharmaceutical Sciences*, 63, No. 5, 721–724 (1974).
C87–081037 English Language Abstract of 62–122671 Japanese Patent, published Jun. 1987.
Joseph A. Capella; *Am. J. Ophthal.*, 74(5): 810–817, 1972.
N. Savion et al; *Metal, Ped., and Syst. Ophthal.* 6: 305–320, 1982.
"Fundamentals and Principles of Ophthalmology", Basic and Clinical Science Course, American Academy of Ophthalmology, pp. 53–56 (1988–1989).
Yue et al., "Growth of Human Corneal Endothelial Cells in Culture", *Investigative Ophthalmology & Visual Science* 30(2):248–253 (1989).

*Primary Examiner*—Jill Warden
*Assistant Examiner*—Sheela J. Huff
*Attorney, Agent, or Firm*—Browdy and Neimark

[57] ABSTRACT

The invention relates to compositions which induce in humans regeneration of the corneal endothelium. The compositions of the invention are of value in regenerating the corneal endothelium in humans, which is frequently damaged in the course of eye surgery and injuries. Such regeneration is very important to ensure the full functionality of the eye. The compositions of the invention comprise as active ingredient an adequate quantity of fibroblast growth factor (FGF) in a suitable physiologically acceptable vehicle. A preferred embodiment of the invention relates to a composition containing a certain quantity of hyaluronic acid and any other viscoelastic agent.

20 Claims, 4 Drawing Sheets

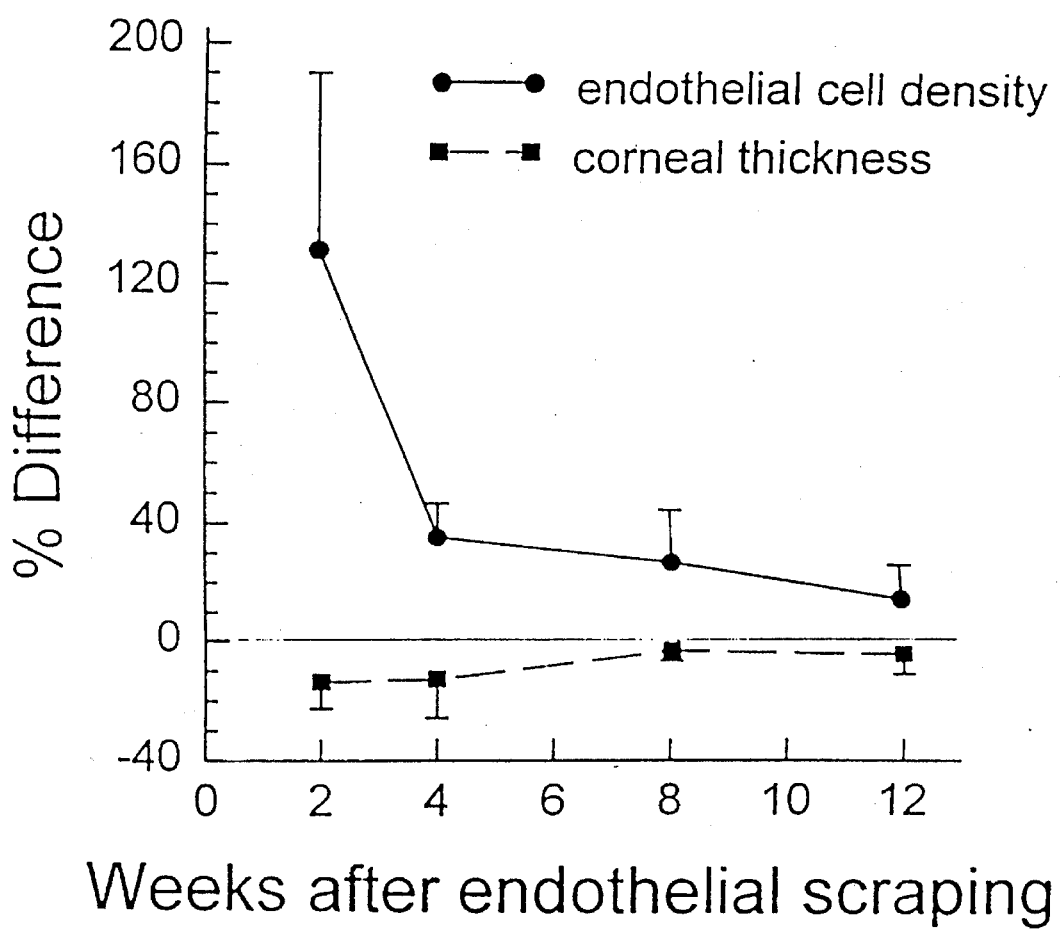

5,510,329

PREPARATIONS FOR THE TREATMENT OF EYES

This application is a continuation of application Ser. No. 07/673,867 filed Mar. 22, 1991 now abandoned, a continuation of application Ser. No. 07/185,893 filed Apr. 26, 1988, now abandoned.

BACKGROUND OF THE INVENTION

The corneal endothelium in humans, primates and carnivores has but a limited regeneration ability. The regeneration of the endothelium is of importance in certain cases, such as for example after accidental or surgical damage to the corneal endothelium or epithelium; it is of importance in cases of degeneration of corneal endothelium, replacing keratoplasty. Fibroblast growth factor has been studied before (see Gospodarowicz et al, *Proc. Nat. Acad. Sci*, USA, 81, 6963–67, 1984 and also Bohlen et al, EMBO J., 4, 1951–56, 1985). It comprises two polypeptides which are basic FGF and Acidic FGF. These can be isolated from bovine brain, from the pituitary and from other organs. Both the acidic and the basic FGF are active in inducing the proliferation of various cultured cells including bovine corneal endothelial cells in culture. The prior art does not allow any valid prediction on the applicability of compositions of the invention for the purposes set out above and for other uses, as will be defined in detail hereinafter.

FIELD OF THE INVENTION

The invention relates to pharmaceutical injectable compositions which induce regeneration of the corneal endothelium in humans. The regeneration of the endothelium, which is frequently damaged during eye surgery, is of importance to ensure a full functioning of the human eye. Spontaneous regeneration of the endothelium in humans is very restricted and thus enhancement of regeneration is of importance.

The compositions of the invention contain as active ingredient a regeneration-inducing quantity of fibroblast growth factor (FGF). Such FGF can be used in different degrees of purity. There can be used crude preparations of the order of 25 µg per 50 µl and up to affinity purified bovine FGF or human recombinant FGF of 0.5 µg in 25 µl of saline. Injection of such preparations results in a significant enhancement of endothelium regeneration. The preparation are advantageously administered into the anterior chamber of the eye within a short period of time after damage is inflicted to the corneal endothelium. Treatment with compositions of the invention enhances endothelial cell density, an improved polygonal shape of the cells, and a reduced thickness of the cornea is attained.

Viscoelastic substances are used routinely in eye surgery for protection and manipulation of tissues and maintenance of spaces. Therefore, a combination of FGF with any viscoelastic substance will not only provide protection to the eye tissue but will also improve the regeneration of the perturbed endothelium. Indeed, improved results are obtained with compositions which contain FGF with a certain quantity of hyaluronic acid or any other viscoelastic substance. Hyaluronic acid at concentrations of the order from 0.1 to 3.0% gave good results, the preferred range being about 0.6 to about 1.2%.

SUMMARY OF THE INVENTION

The invention relates to pharmaceutical ophthalmological compositions which induce regeneration of the corneal endothelium in humans. The use of such compositions is of importance in a wide range of ophthalmological situations, such as:

a. After surgical or accidental injury to the corneal endothelium stroma or epithelium;

b. as a protective agent for use before, during and after surgery of the anterior chamber for the eye such as cataract extraction, keratoplasy, etc. and as growth enhancer after such procedures;

d. to improve donor corneal endothelium preservation prior to keratoplasy;

e. for growth enhancement of any relevant occular tissue during and after injury and various types of disease.

The pharmaceutical compositions of the invention comprise as active ingredient fibroblast growth factor (FGF), containing about 0.5 to 25 µg/eye of FGF, depending on the purity of the preparation, in a suitable buffer system, advantageously together with an aqueous viscoelastic composition such as hyaluronic acid sodium salt, methylcellulose, chondroitin sulfate, water-soluble collagen extract and the like. These additives ought to be used in a suitable concentration providing the desired degree of viscosity and adherence, and generally this will be in the range of from about 0.1% and 10%, preferably about 1%. The compositions of the present invention ought to be at a certain pH, generally in the range of pH 6.75 to pH 7.75, preferably about pH 7.40.

The adjustment of the pH can be attained by the use of any of the conventional ophthalmological buffers. There may be used, for example, Dulbecco's modified phosphate buffered saline (PBS), balanced salt solution (BSS) or BBS Plus, which is supplemented with gluthathione, glucose and with bicarbonate buffer. The regeneration of damaged endothelium does not take place spontaneously, or at least not in an adequate manner and at an adequate rate. The compositions of the present invention overcome this problem to a large extent. These contain, as set out above, a regeneration inducing quantity of FGF, adapted to induce endothelial growth in vivo in the human eye.

The sterile liquid compositions are generally applied by injection. The compositions of the invention are of special value in cases of occular trauma and after corneal implantations where grave damage to the endothelial is very frequent. Proper endothelia function is essential for corneal transparency, and the speedy recovery of this layer is of paramount importance. This applies to surgery for cataract eye repairs.

Although it has been previously shown the FGF has a beneficial effect in the repair process of corneal endothelium of bovine corneas in vitro (Savion et al., *Metab. Pediat. Syst. Ophthal.*, 1982, 6 305), this could not allow a valid prediction on the activity of FGF in vivo in the human eye in cases of situations as set out above.

The ophthalmological compositions of the present invention have a specially advantageous activity when they also contain a viscoelastic component. There may be used a variety of such constituents; best results were obtained with a certain percentage of hyaluronic acid or a salt thereof. With hyaluronic acid sodium salt concentrations of from about 0.1% to about 3.0% gave good results, the preferred content being from about 0.5 to about 1.2 per cent. Experiments were carried out in vivo first without corneal endothelium by scraping off the endothelium of the Descemet's membrane by a specially designed instrument. FGF solutions of the invention, comprising either a simple carrier (buffer) a protein carrier (bovine albumin) or a viscoelastic additive in combination with a suitable buffer were used. The compositions were administered by injection and significant enhancement of endothelium regeneration was observed by comparison with controls. During the first two weeks after scraping-off of the layer and injection of the preparation, the endothelial cell density (ECD) in FGF-treated eyes was higher by a factor of 1.7 to 2.3 compared with controls. The application of FGF resulted furthermore in an improvement of the shape of the cells: the treated layer had well-defined polygonal cells, with a decreased thickness of the cornea.

DETAILED DESCRIPTION OF THE INVENTION

Figure 1B:
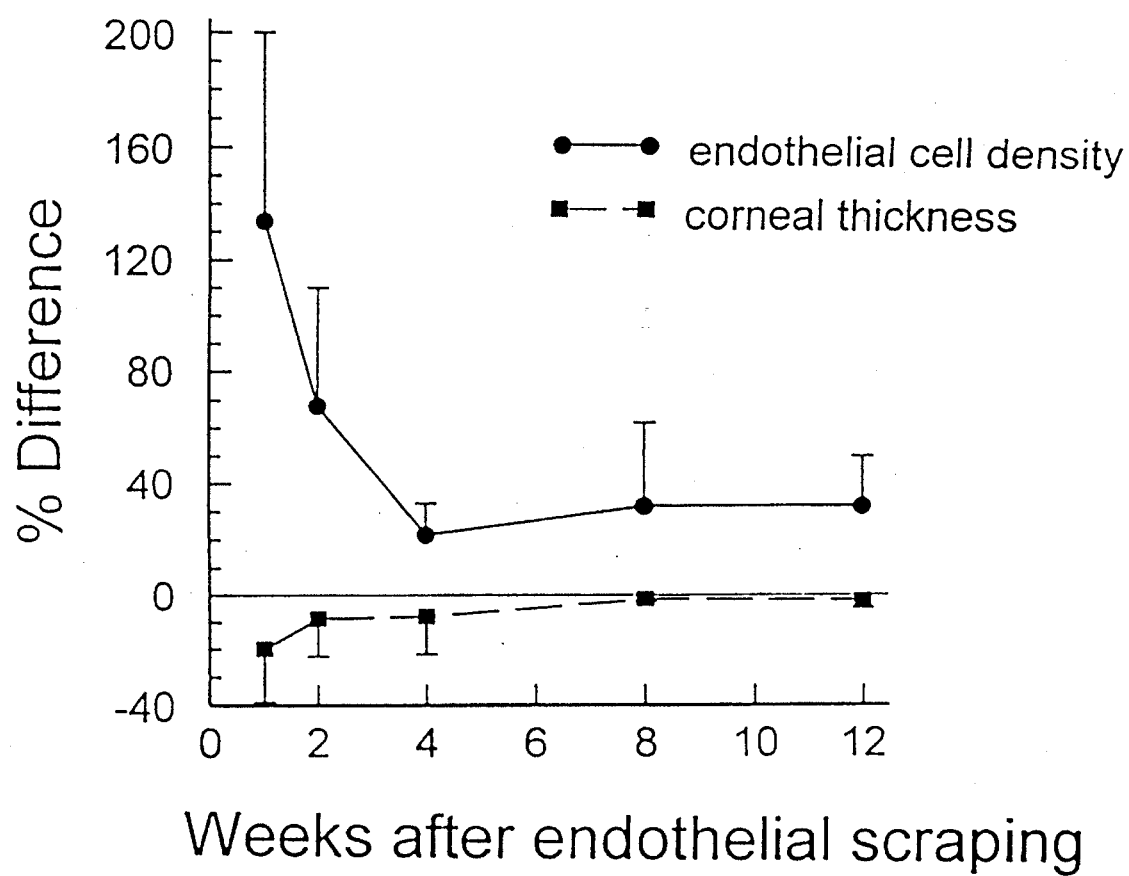
FIG. 1 (A,B) shows the effect of FGF on regeneration of corneal endothelial cells.
Figure 2A:
FIG. 2 (A–D) shows morphology of regeneration of corneal endothelium in the presence or absence or FGF.
Figure 2B:
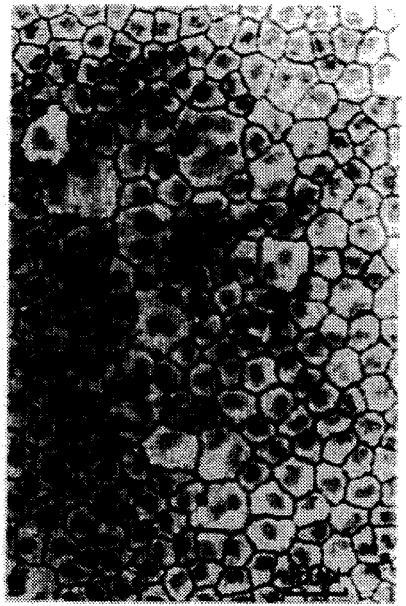
Figure 2C:
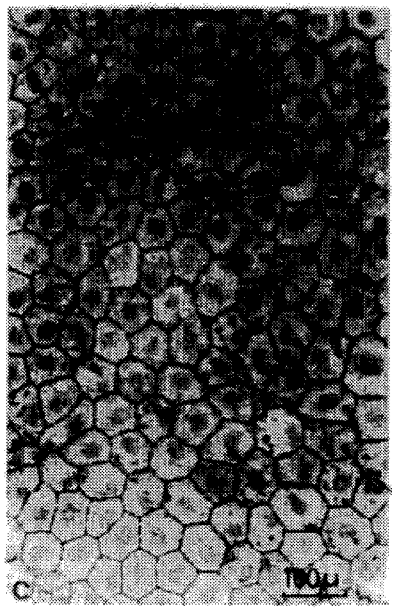
Figure 2D:
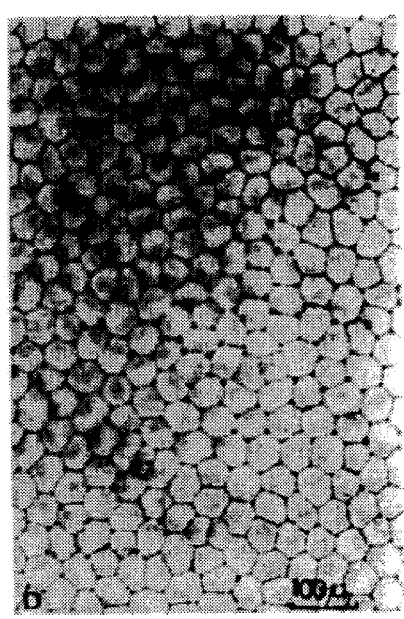

The following detailed description is by way of illustration and ought not to be construed in a limitative manner.

MATERIALS AND METHODS

Materials:

Crude fibroblast growth factor (FGF) was prepared from bovine brain as previously described (Gospodarowicz et al. Journal Biol. Chem. 253, 3736–43 (1978) Highly purified brain FGF was prepared by heparin-Sepharose affinity chormatography (Gospodarowicz et al. *Proc. Nat. Acad. Sci* USA 81 6963–67, 1984).

Purification of FGF—Unless otherwise indicated, all operations were performed at 0°–5° C. For kilograms of frozen bovine brain were thawed and homogenized in a Waring Blendor with 8 liters of water containing 0.15M $(NH_4)_2SO_4$. The crude homogenate was adjusted to pH 4.5 with HCl and was stirred for 2 h. The homogenate was then centrifuged at 23,000×g for 45 min to remove cells and debris. The supernatant was adjusted to a pH of 6.5 to 7.9 by the addition of 1N NaOH. Two hundred grams of $(NH_4)_2SO_4$ were added per liter and the suspension was centrifuged at 23,000×g for 20 mim. The pellet, which contained little FGF activity, was discarded. An additional 250 g of $(NH_4)_2SO_4$/liter was added to the supernatant. The suspension was then centrifuged at 23,000× for 20 min. The supernatant was discarded and the pellet which contained 35 g of proteins (Table I) and most of the FGF activity was collected and dissolved in 20 ml of cold, distilled water. The solution was dialyzed against 20 liters of water for at least 15 h with two changes of water. The pH of the dialysate was adjusted to pH 6.0 with 0.1M formic acid, and its conductivity was checked to make sure that the ionic strength did not exceed that of a solution of 0.1M sodium phosphate, pH 6.0 . The solution was then centrifuged for 10 min at 23,000× g to remove any precipitate. The dialysate was then applied on a column (3×20 cm) of carboxymethyl-Sephadex C-50 equilibrated with 0.1M sodium phosphate, pH 6.0. The column was washed with 0.1M sodium phosphate, pH 6.0. Eighty percent of the material (Fraction $F_4$) passed through the column unadsorbed. It did not contain more than 10% of the initial mitogenic activity. Elution with 0.1M sodium phosphate, 0.15M NaCl removed a fraction with a very low FGF activity (Fraction $F_2$). Most of the FGF activity was eluted with 0.1M sodium phosphate, 0.5M NaCl at pH 6.0. This eluted fraction was concentrated to about 10 ml by pressure ultrafiltration (UM-10 membrane).

Isolation of Brain and Pituitary FGF Bovine brains (4 kg) or pituitaries (1.8 kg) were extracted with 0.15M ammonium sulfate (pH 4.5) as described (1.3.4). Partially purified FGF was prepared by ammonium sulfate precipitation and batch adsorption/elution, using carboxymethyl Sephadex C-50, as described (3,4). FGF-containing fractions eluting from the ion-exchange column with 0.6M NaCl/0.1M sodium phosphate, pH 6.0 were pumped (35 ml/hr) through a heparin-Sepharose column (1.6×5 cm; bed vol. 10 ml) that had been equilibrated at room temperature with 10 mN Tris-HCl, pH 7.0/0.6M NaCl. The column was washed (flow rate 35 ml/hr) with 10 mM Tris-HCl, pH 7.0/1.1M NaCl, until the absorbance of the eluate at 280 nm became negligible. Mitogenic activity was then eluted with a linear 2 hr salt gradient of 1.1M to 2M NaCl in 10 mN Tris-HCl (pH 7.0) at 35 ml/hr. Fractions with biological activity were pooled and kept frozen at −80° C. Unless otherwise stated, total protein was determined by the dye fixation assay, using bovine serum albumin as a standard and/or by amino acid analysis.

Scraping of the Corneal Endothelium

Street cats weighing 2.4 to 3.6 kg were anesthetized by intramuscular injection of ketamine (0.25 mg/kg) followed by intravenous injection of phenobarbitone sodium (2.5 mg/kg) and subcutaneous administration of atropine sulfate (0.015 mg/kg). Corneal endothelium scraping was performed in both eyes as previously described (Landshman et al. 1985). Briefly, the anterior chamber was opened at the limbus, the lower arm of chalazion forceps, with a mobile methylmethacrylate disc attachment (8 mm in diameter), was brought in close contact with the corneal endothelium and the disc was then rotated 30° around its own axis. This maneuver caused scraping of all the endothelial cells in contact with the methylmethacrylate segment without injuring the Descemet's membrane. After removal of the instrument, the wound was closed with 5-0 nylon sutures, and 5% chloramphenicol ointment was applied to the conjunctival sack.

Treatment:

Crude fibroblast growth factor (FGF), 25 µg in 50 µl of phosphate buffer saline (PBS), or affinity purified FGF, 0.5 µg in 25 µl of PBS containing 0.5% BSA as an irrelevant carrier protein were injected into the anterior chamber of one of the eyes, while 50 µl PBS or 25 µl of PBS containing 0.5% BSA were injected into the other eye, respectively. For this purpose, the eye was perforated by a 25 gauge needle near the limbus, and 50 µl or 25 µl of aqueous humor was drawn off from the anterior chamber and replaced by similar volumes of FGF or the control PBS solution alone. The FGF and PBS injections were done immediately after the operation and in some cases were repeated 1 and 2 weeks later.

Follow-Up:

The animals were examined preoperatively and 4.8 and 12 weeks after the operation using a specular microscope (Heyer Schulte Medical Optics Center, Model CEM-4) for determining central endothelial cell density (ECD) and central corneal thickness. Since specular microscope investigations are impossible or very difficult during the first 2 postoperative weeks because of marked corneal edema, during this time ECD was determined using flat preparations of whole cornea (Matsubara and Tanishima, *Jap.J.Ophth.* 26 264–78, (1982) and corneal thickness was determined by slit lamp pachometry (SL-50, Topcon).

Histological Procedures:

For the determination of ECD during the first 2 weeks after operation, the eyes were enucleated, the corneas were cut out and impregnated with silver, and corneal endothelial flat preparations were made (Matsubara and Tanishima, *Jap.J. Ophth.* 26 264–73, 1982). The central part of the corneal endothelium was photographed and six squares, 100 and 100 µ each, were randomly selected from the micrograph. In each square the number of cells was calculated, Mean±standard deviation were determined and the results were multiplied by 100 for determination of the number of cells in 1 mm$^2$ (e.g. endothelial cell density). In order to study the morphology of the regenerating endothelium, the eyes were enucleated 2,12 and 21 weeks after operation and the corneas were cut out and impregnated by silver. The endothelium was then removed, stained by Harris's hematoxylin and flat preparations were made (Oh, 1963). The polygonality of endothelial cells was studied by calculating its values along 200 cells in the central part of each cornea in these preparations.

RESULTS:

Effect of FGF on Endothelial Cell Density:

The corneal endothelium of cats was scraped and crude FGF (FIG. IA; 25 µg per eye) or affinity purified FGF (FIG. IB; 0.5 µg per eye) were injected into the anterior chamber of one of the eyes of each cat, while PBS was injected into the other eye as a control. In the case of affinity purified FGF the PBS contained 0.5% BSA both in the presence of FGF and in the control eye. The regeneration of the endothelium in the crude and purified FGF treated as well as the control eyes was followed for a period of 12 weeks by measuring the corneal thickness and the endothelial cell density (ECD). The percent difference in ECD and in corneal thickness between the FGF treated eye and the control eye in each cat was calculated, and the means±S.D. of 4 to 12 cats in each point is presented in FIG. 1. The data indicate a significant increase in ECD in FGF-treated eyes whether a crude FGF (FIG. 1,A) or affinity purified FGF (FIG. 1,B) was used. The difference between the control and the FGF-treated eyes was most obvious in the first 2 weeks. The ECD was higher in the crude FGF-treated eyes compared to control eyes by a factor of 2.31±0.58 ($p<0.01$) after 2 weeks (FIG. 1A). During the following weeks (up to 12 weeks after the operation) the difference in ECD between the crude FGF-treated and control eyes decreased to a factor of 1.14±0.11 to 1.37±0.20, but it was still statistically significant ($p<0.05$). In the case of affinity purified FGF (FIG. 1B), the ECD was increased by a factor of 2.35±0.68 ($p<0.01$) and 1.70±0.39 (p 0.01) when measured one and two weeks after the operation, respectively.

During the following period of 4 to 12 weeks after the operation the ECD in the affinity purified FGF-treated eyes remained higher by a factor of 1.21±1.11 to 1.33±1.23 (p 0.05).

Effect of FGF on Corneal Thickness:

The corneal thickness in crude FGF-treated eyes was significantly lower than that of the control eyes during the first 4 post-operative weeks (12.7±2.9 to 13.6±8.8; p 0.02) but with time this difference became insignificant (FIG. 1A). As was the case with ECD the effects of the crude FGF and the affinity purified FGF on corneal thickness were very close (FIG. 1B).

Figure 3:
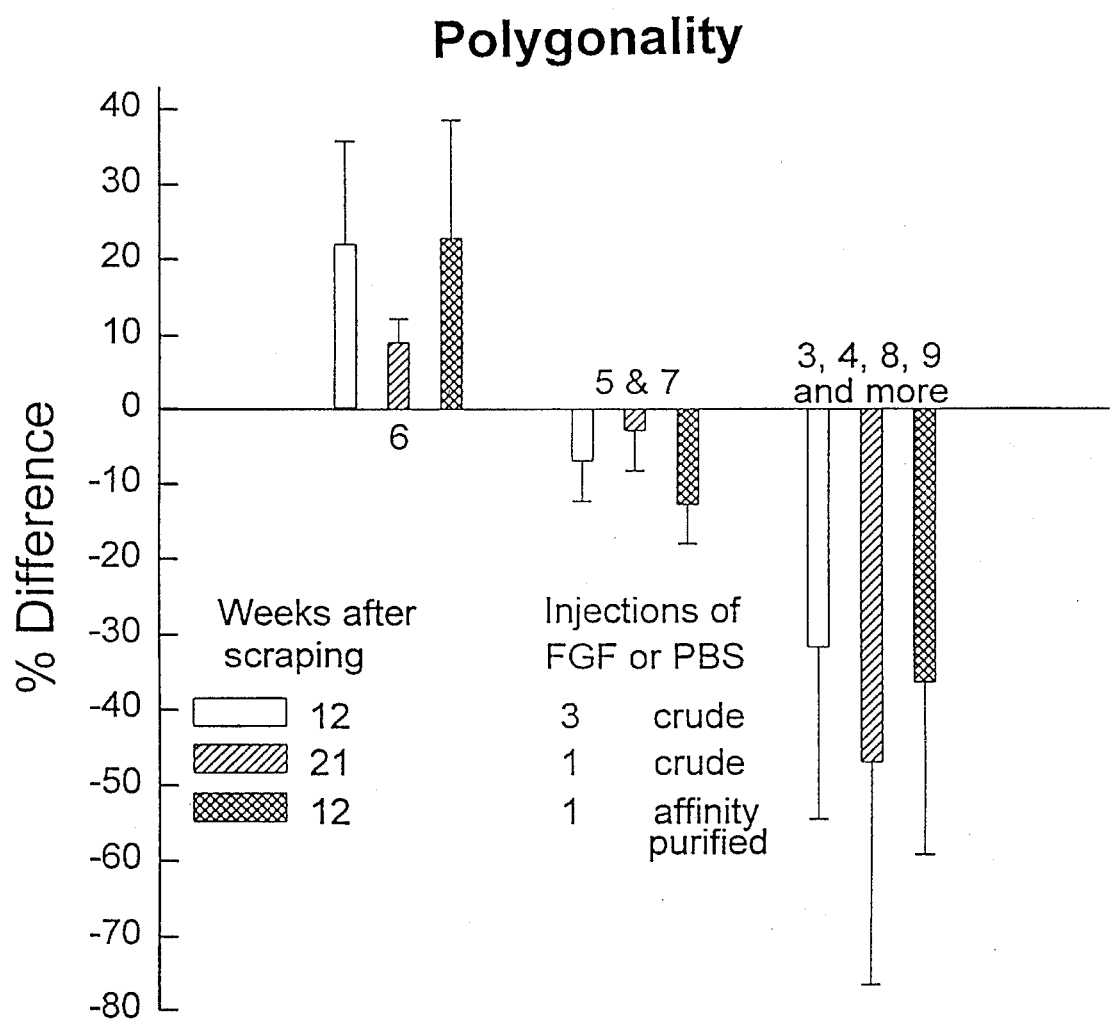
FIG. 3 shows the effect of FGF on the polygonal shape of regenerating corneal endothelial cells.

Morphology of the Regenerating Endothelium:

FGF demonstrated a significant effect on the morphological appearance of the regenerating corneal endothelium (FIG. 2). Two weeks after scraping most of the cells in crude FGF-treated eyes were smaller and had a more regular appearance than those in the control lesions. After 21 weeks the corneal endothelial cells in crude FGF-treated eyes had a morphology close to that of normal endothelium, while the endothelial cells in the controllesions still demonstrated a highly abnormal appearance. Similar morphology was observed when affinity purified FGF was used (data not shown). The effect of FGF on cell morphology was further evaluated by studying the polygonal shape of the cells 12 and 21 weeks after operation (FIG. 3). In FGF-treated eyes the number of hexagonal cells increased by 9±4% to 22±17% $p<0.05$), and the number of cells with a low or a very high number of sides was significantly decreased by 32.1±22.2 to 48.1±27.8% ($p<0.05$). Similar effects were observed when crude FGF and affinity purified FGF were used.

Histological studies of the corneas treated with FGF revealed no differences from the control corneas in the number and morphology of the blood vessels in the stroma (data not shown).

Effects of Multiple Injections:

In order to quantitate the required FGF dose, we tested the effect of 3 FGF injections as well. Crude FGF was injected immediately after the operation and repeated 1 and 2 weeks later. The three consecutive injections of crude FGF, did not improve the increase in ECD, the decrease in corneal thickness (data not shown) and the polygonality of the cells (FIG. 3) above the significant effect observed after one injection of FGF.

Similar experiments were carried out with identical solutions, as set out above, but which contained instead of the carrier protein, a viscoelastic agent.

There were used compositions containing from about 0.1% to about 3% by weight of hyaluronic acid. Other solutions were tested which contained agents such as methylmethoxy cellulose, collagens or the like.

The viscoelastic agents enhance adhesion of the preparation to the tissues where such composition is applied to, and thus an enhanced localized effect is attained.

LEGENDS TO FIGURES

FIG. 1 (A, B) Effect of FGF on the Regeneration of Corneal Endothelial Cells and on Corneal Thickness:

The corneal endothelium was scraped in both eyes of each cat as described under "Materials and Methods". At the end of the operation crude FGF in PBS solution was injected to the anterior chamber of one of the eyes and PBS alone was injected in the second eye as a control (A).

In part of the cats the effect of affinity purified FGF in PBS containing 0.5% BSA was tested, and in these cases PBS containing 0.5% BSA was injected to the control eyes (B). The animals were examined preoperatively and 4,8 and 12 weeks after operation using a specular microscope for determining corneal endothelial cell density (ECD) and central corneal thickness. During the first two weeks after the operation the corneal thickness was measured by slit-lamp pachometry and the ECD was determined by cornea flat preparations. The figure presents the percentage of differences in ECD (—) and in corneal thickness (----) between the FGF treated eyes to the control eyes. Each point represents the mean±S.D. obtained from 4 to 12 cats.

FIG. 2 (A–D) Morphology of the Regeneration Corneal Endothelium in Presence or Absence of FGF:

Two weeks (A,B) and 21 weeks (C,D) after corneal endothelial scraping, eyes treated once with crude FGF (B,D) or PBS (A,C) were enucleated. Corneal flat preparations and endothelial flat preparations were made from eyes enucleated 2 and 21 weeks after endothelial scraping, respectively. The central part of the corneal endothelium is photographed and presented.

FIG. 3 Effect of FGF on the Polygonal Shape of Regenerating Corneal Endothelial Cells:

Eyes treated three times with crude FGF or PBS were enucleated 12 weeks after operation and eyes treated only once with either crude FGF or highly purified FGF were enucleated 21 weeks after operation, respectively. The corneas were excised and endothelial flat preparations were made. The polygonal shape of the endothelial cells was studied by counting the number of sides of 200 cells in the central part of each cornea. Each bar in the figure represents the percentage of difference (means±S.D.) between FGF-treated eyes and PBS-treated eyes obtained from 4 to 12 cats.

We claim:

1. A method for enhancing the regeneration of the corneal endothelium in an eye of a human patient in need of said regeneration, comprising administering one injection into the anterior chamber of said human eye of an effective quantity of a composition containing a fibroblast growth factor in a physiologically acceptable carrier.

2. The method according to claim 1 wherein said composition contains a component enhancing the viscosity and adherence of the preparation to the eye to which the composition is applied.

3. The method according to claim 2 wherein the component enhancing the viscosity and adherence is selected from the group consisting of hyaluronic acid salts, chondroitin sulfate, methyl cellulose and water-soluble collagen extracts.

4. The method according to claim 2 wherein the component enhancing the viscosity and adherence is present in an amount of from about 0.1% to about 10% by weight of the total composition.

5. The method according to claim 1 wherein the composition contains from about 0.1 to about 2 µg/eye of affinity purified fibroblast growth factor or human recombinant fibroblast growth factor.

6. A method for protecting the corneal endothelium in the eye of a human patient in need of said protection against degeneration caused by surgery to the eye, comprising administering one injection into the anterior chamber of said eye of an effective quantity of a composition containing a fibroblast growth factor in a physiologically acceptable carrier.

7. The method according to claim 6 wherein said composition contains a component enhancing the viscosity and adherence of the preparation to the eye to which the composition is applied.

8. The method according to claim 7 wherein the component enhancing the viscosity and adherence is selected from the group consisting of hyaluronic acid salts, chondroitin sulfate, methyl cellulose and water-soluble collagen extracts.

9. The method according to claim 7 wherein the component enhancing the viscosity and adherence is present in an amount of from about 0.1% to about 10% by weight of the total composition.

10. The method according to claim 6 wherein the composition contains from about 0.1 to about 2 µg/eye of affinity purified fibroblast growth factor or human recombinant fibroblast growth factor.

11. A method for enhancing healing of the corneal endothelium in a human patient needing treatment for an injured or diseased eye comprising administering one injection into the anterior chamber of said injured or diseased eye of an effective quantity of a composition containing a fibroblast growth factor in a physiologically acceptable carrier.

12. The method according to claim 11 wherein said composition contains a component enhancing the viscosity and adherence of the preparation to the eye to which the composition is applied.

13. The method according to claim 12 wherein the component enhancing the viscosity and adherence is selected from the group consisting of hyaluronic acid salts, chondroitin sulfate, methyl cellulose and water-soluble collagen extracts.

14. The method according to claim 12 wherein the component enhancing the viscosity and adherence is present in an amount of from about 0.1% to about 10% by weight of the total composition.

15. The method according to claim 11 wherein the composition contains from about 0.1 to about 2 µg/eye of affinity purified fibroblast growth factor or human recombinant fibroblast growth factor.

16. A method for enhancing regeneration of transplanted corneal endothelium tissue which has been transplanted into the eye of a human patient comprising injecting into the anterior chamber of said eye an effective amount to enhance regeneration of said transplanted corneal endothelium tissue of a preparation containing fibroblast growth factor in a physiologically acceptable carrier.

17. The method according to claim 16 wherein said composition contains a component enhancing the viscosity and adherence of the preparation to the eye to which the composition is applied.

18. The method according to claim 17 wherein the component enhancing the viscosity and adherence is selected from the group consisting of hyaluronic acid salts, chondroitin sulfate, methyl cellulose and water-soluble collagen extracts.

19. The method according to claim 17 wherein the component enhancing the viscosity and adherence is present in an amount of from about 0.1% to about 10% by weight of the total composition.

20. The method according to claim 16 wherein the composition contains from about 0.1 to about 2 µg/eye of affinity purified fibroblast growth factor or human recombinant fibroblast growth factor.

* * * * *